(12) United States Patent
Kitagawa (10) Patent No.: US 7,365,842 B2
(45) Date of Patent: Apr. 29, 2008

(54) LIGHT SCANNING TYPE CONFOCAL MICROSCOPE

(75) Inventor: Junichi Kitagawa, Musashino (JP)

(73) Assignee: Olympus Corporation, Tokyo (JP)

( * ) Notice: Subject to any disclaimer, the term of this patent is extended or adjusted under 35 U.S.C. 154(b) by 191 days.

(21) Appl. No.: 11/154,968

(22) Filed: Jun. 16, 2005

(65) Prior Publication Data

US 2005/0286048 A1    Dec. 29, 2005

(30) Foreign Application Priority Data

Jun. 24, 2004    (JP) .............................. 2004-186348

(51) Int. Cl.
*G01J 3/18*     (2006.01)
*G01J 3/26*     (2006.01)
*G01J 3/32*     (2006.01)
*G01J 3/443*    (2006.01)
*G01J 3/04*     (2006.01)

(52) U.S. Cl. ................. 356/317; 356/329; 356/332; 356/334

(58) Field of Classification Search .......... 356/317, 356/329, 332, 334
See application file for complete search history.

(56) References Cited

U.S. PATENT DOCUMENTS

| | | | | |
|---|---|---|---|---|
| 4,084,909 A | * | 4/1978 | Mathisen .................... 356/332 |
| 4,113,384 A | * | 9/1978 | Lauer et al. ................. 356/70 |
| 4,243,882 A | * | 1/1981 | Yasujima et al. ....... 250/339.06 |
| 4,707,838 A | * | 11/1987 | Reule et al. ............. 372/38.07 |
| 4,804,271 A | * | 2/1989 | Cammann .................. 356/416 |
| 5,192,980 A | | 3/1993 | Dixon et al. |
| 5,194,912 A | * | 3/1993 | Batchelder et al. ......... 356/301 |
| 5,491,582 A | * | 2/1996 | Fujita ..................... 359/341.1 |
| 5,510,894 A | * | 4/1996 | Batchelder et al. ......... 356/301 |
| 5,710,663 A | * | 1/1998 | Kawasaki ................... 359/389 |
| 5,886,784 A | * | 3/1999 | Engelhardt ................. 356/326 |
| 6,262,837 B1 | * | 7/2001 | Nagano et al. ............. 359/368 |
| 6,555,811 B1 | * | 4/2003 | Amos ........................ 250/234 |
| 6,594,074 B1 | * | 7/2003 | Wolleschensky et al. ... 359/385 |
| 6,809,815 B2 | * | 10/2004 | Knebel ...................... 356/308 |

(Continued)

OTHER PUBLICATIONS

Dickenson, Bearman, Tille, Lansford, and Fraser, "Multispectral Imaging and Linear Unmixing Add a Whole New Dimension to Laser Scanning Microscopy", 2001, BioImaging, vol. 31, No. 6.*

*Primary Examiner*—Gregory J. Toatley, Jr.
*Assistant Examiner*—Bryan J Giglio
(74) *Attorney, Agent, or Firm*—Frishauf, Holtz, Goodman & Chick, P.C.

(57) ABSTRACT

A light scanning type confocal microscope includes a light source unit that projects an excitation light beam, a scanning optical system that scans the excitation light beam, an objective lens that applies the excitation light beam to a sample, a separation optical element that separates the excitation light and detection light generated by the sample, a confocal detection unit that obtains a confocal effect, and a spectral detection device that spectrally detects the detection light. The spectral detection device has a spectroscopic element that spectrally separates the detection light, a light extracting unit that extracts light in a wavelength band from the light spectrally separated by the spectroscopic element, a detector that detects the light extracted by the light extracting unit, and a wavelength band shifting unit that shifts a wavelength band of light to be extracted by the light extracting unit.

16 Claims, 7 Drawing Sheets

U.S. PATENT DOCUMENTS

| | | | |
|---|---|---|---|
| 7,002,680 B2 * | 2/2006 | Kaneko | 356/308 |
| 7,099,003 B2 * | 8/2006 | Saptari et al. | 356/319 |
| 7,102,746 B2 * | 9/2006 | Zhao | 356/301 |
| 7,212,285 B2 * | 5/2007 | Goto et al. | 356/328 |
| 7,218,762 B2 * | 5/2007 | Olschewski | 382/128 |
| 7,253,897 B2 * | 8/2007 | Moon et al. | 356/328 |
| 2002/0020819 A1 | 2/2002 | Wolleschensky et al. | |
| 2003/0191398 A1 * | 10/2003 | Motz et al. | 600/478 |
| 2004/0073120 A1 * | 4/2004 | Motz et al. | 600/478 |
| 2005/0046836 A1 * | 3/2005 | Olschewski | 356/318 |

* cited by examiner

LIGHT SCANNING TYPE CONFOCAL MICROSCOPE

CROSS-REFERENCE TO RELATED APPLICATIONS

This application is based upon and claims the benefit of priority from prior Japanese Patent Application No. 2004-186348, filed Jun. 24, 2004, the entire contents of which are incorporated herein by reference.

BACKGROUND OF THE INVENTION

1. Field of the Invention

The present invention relates to a light scanning type confocal microscope in which excitation light is applied to a sample while being scanned and fluorescence exiting from the sample is detected.

2. Description of the Related Art

In recent years, along with development in fluorescence reagents, the functions of a laser scanning type confocal microscope (CLSM) increase. In addition to conventional fluorescence detection using a filter, a scheme of spectrally detecting fluorescence generated by a sample has become available. With fluorescence spectral detection, the fluorescence spectrum unique to each reagent can be quantitatively analyzed in more detail. Also, fluorescence observation is performed with a sample obtained by combining fluorescence reagents having large cross talk in their wavelength characteristics. A demand has arisen for observation of the individual fluorescence separately.

U.S. patent application Publication No. 2002/0020819A1 discloses an apparatus that spectrally detects fluorescence that is generated by a sample excited by a laser beam. More specifically, this apparatus spectrally separates fluorescence generated from the sample with a dispersion element of a diffraction grating, and detects the spectral fluorescence by a multi-channel detector. The multi-channel detector comprises detection channels, which are separated physically. The dispersed fluorescence is spatially distributed into the individual channels, and each distributed fluorescence is separated in its wavelength region and detected. Therefore, each channel has a minimal wavelength band width. The spectral profile of the fluorescence is acquired by electrically identifying the detection position of each channel or moving the detection position.

U.S. Pat. No. 6,809,815 discloses another apparatus that spectrally detects fluorescence. According to this apparatus, among fluorescence that is dispersed by a dispersion element comprising a prism, the fluorescence in a wavelength band that depends on the aperture width of a slit is detected. When at least one optical component on the optical path is rotated or slid, (the central wavelength of) the wavelength band is changed. Thus, a spectral profile is acquired.

U.S. Pat. No. 5,192,980 discloses still another apparatus that spectrally detects fluorescence. According to this apparatus, the fluorescence is dispersed by a dispersion element comprising a diffraction grating. A pinhole formed in front of a detector obtains a confocal effect and selects the wavelength. When the dispersion element is rotated in the same manner as in U.S. Pat. No. 6,809,815, the wavelength is selected by the pinhole within a desired region. A very narrow wavelength width is selected in accordance with the size of the pinhole, and highly accurate spectral detection is performed.

BRIEF SUMMARY OF THE INVENTION

A light scanning type confocal microscope according to the present invention comprises a light source unit that projects an excitation light beam, a scanning optical system that scans the excitation light beam, an objective lens that applies the excitation light beam to a sample, a separation optical element that separates the excitation light applied to the sample and detection light (including fluorescence and reflected light) generated by the sample upon application of the excitation light, a confocal detection unit that obtains a confocal effect, and a spectral detection device that spectrally detects the detection light. The spectral detection device has a spectroscopic element that spectrally separates the detection light, a light extracting unit that extracts light in a wavelength band having an arbitrary width from the light spectrally separated by the spectroscopic element, a detector that detects the light extracted by the light extracting unit, and a wavelength band shifting unit that shifts a wavelength band of light to be extracted by the light extracting unit.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

The embodiments of the present invention will be described below with reference to the views of the accompanying drawing.

First Embodiment

Figure 1:
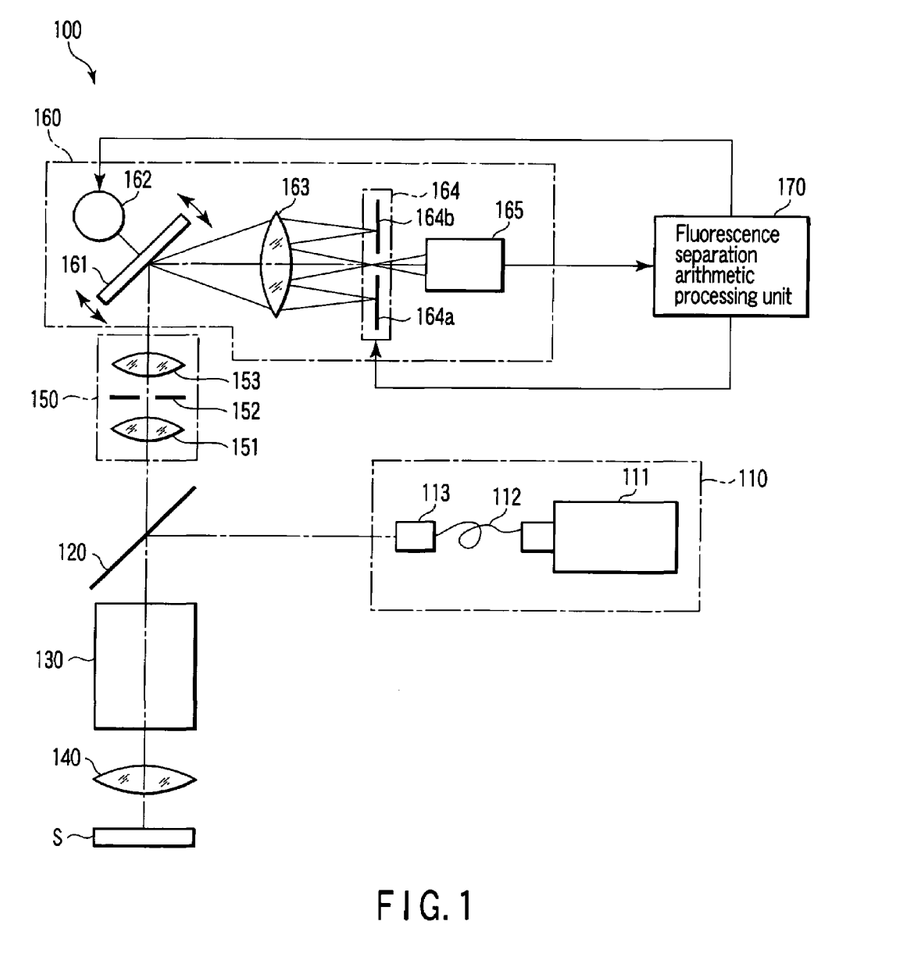
FIG. 1 schematically shows the arrangement of a laser scanning type confocal microscope according to the first embodiment of the present invention.

FIG. 1 schematically shows the arrangement of a laser scanning type confocal microscope according to the first embodiment of the present invention.

A laser scanning type confocal microscope 100 of the first embodiment comprises a light source unit 110 for projecting an excitation light beam, a scanning optical system 130 for scanning the excitation light beam from the light source unit 110, an objective lens 140 for applying the excitation light beam to a sample S, a dichroic mirror 120 serving as a separation optical element for separating excitation light applied to the sample S and detection light (including fluorescence and reflected light) generated by the sample S upon application of the excitation light, a confocal detection unit 150 for obtaining a confocal effect, and spectral detecting means or a spectral detection device 160 for spectrally detecting the detection light.

The light source unit 110 has a laser source 111 that generates the excitation light, an optical fiber 112 that transmits the excitation light generated by the laser source 111, and a projection unit 113 that projects the excitation light transmitted by the optical fiber 112 as an excitation light beam.

The scanning optical system 130 comprises a known scanning element, e.g., a galvanomirror or acoustic optical element, which scans a light beam.

The confocal detection unit 150 is located on the optical path between the dichroic mirror 120 and spectral detection device 160. For example, the confocal detection unit 150 has two convex lenses 151 and 153 and a pinhole 152 arranged between the convex lenses 151 and 153. The pinhole 152 is arranged at a position confocal with the focal point (convergent point) of the excitation light converged by the scanning optical system 130 and objective lens 140 through the objective lens 140, scanning optical system 130, and convex lens 151. Thus, the confocal detection unit 150 selectively extracts, from detection light separated by the dichroic mirror 120, detection light emitted from a sample plane (a plane in the sample) that is located at a specific height along the optical axis.

The spectral detection device 160 has a dispersion element 161 that deflects the detection light in different directions in accordance with the wavelengths, rotary means or a rotary device 162 for rotating the dispersion element 161 about an axis perpendicular to the optical axis, a convergent lens 163 for converging the detection light spectrally separated by the dispersion element 161, a slit 164 serving as a mechanical variable aperture that can change its aperture width, and detecting means or a detector 165 for detecting the light extracted by the slit 164.

The slit 164 serves as light extracting means or a light extracting portion for extracting light in a wavelength band having an arbitrary width from the light spectrally separated by the dispersion element 161. The slit 164 has two light-shielding plates 164a and 164b, which define the slit width, e.g., aperture. Both the two light-shielding plates 164a and 164b are allowed to move in directions perpendicular to the optical axis and determine the upper and lower limits of the wavelength band of the light to be extracted. Namely, the slit 164 can freely change the width of the wavelength band of the light to be extracted.

The dispersion element 161 serves as spectroscopic means or a spectroscopic element for spectrally separating the detection light. The dispersion element 161 is not limited to this and comprises, e.g., a diffraction grating. In this case, the detection light is spectrally separated as it is diffracted at an angle of diffraction corresponding to its wavelength. The dispersion element 161 is not limited to a diffraction grating but may comprise an arbitrary optical element having a spectroscopic function, e.g., a prism. In this case, the detection light is spectrally separated as it is refracted at an angle of refraction corresponding to its wavelength. FIG. 1 shows a case wherein the dispersion element 161 comprises a diffraction grating. When the dispersion element 161 comprises a prism, the positions of the convergent lens 163, slit 164, and detector 165 must be different from those in FIG. 1 due to the difference between diffraction and refraction. Except for this, the arrangement of this embodiment can be directly employed.

The rotary device 162 serves as wavelength band shifting means or a wavelength band shifting unit for shifting the wavelength band of the light to be extracted by the slit 164. More specifically, the rotary device 162 rotates the dispersion element 161 to shift the typical wavelength (e.g., the central wavelength, lower-limit wavelength, or upper-limit wavelength) of the wavelength band of light that can be transmitted through the slit 164 by a predetermined shift amount. The rotary device 162 is not limited to this and comprises, e.g., a galvanometer or stepping motor.

The detector 165 is not limited to the one employed in the first embodiment but preferably comprises a high-sensitivity detector, e.g., a photomultiplier.

The laser scanning type confocal microscope 100 further comprises fluorescence separation arithmetic processing means or a fluorescence separation arithmetic processing unit 170 that separately calculates fluorescence information corresponding to the spectral component of each type of the fluorescence from the fluorescence information (fluorescence spectral image or fluorescence characteristic data) obtained by the spectral detection device 160.

Referring to FIG. 1, the excitation light beam projected from the light source unit 110 is reflected by the dichroic mirror 120 and applied to the sample S through the scanning optical system 130 and objective lens 140. The sample S is dyed with fluorescent dyes, which generate fluorescence upon application of the excitation light. The detection light (usually contains different types of fluorescence and reflected light) from the sample S passes through the objective lens 140 and scanning optical system 130 and is transmitted through the dichroic mirror 120, so as to be separated from the excitation light. The detection light then enters the confocal detection unit 150. The detection light transmitted through the dichroic mirror 120 passes through the confocal detection unit 150 to appear as detection light from only a plane that is at a specific height in the sample S, and enters the spectral detection device 160.

The detection light entering the spectral detection device 160 is spectrally separated as it is deflected by the dispersion element 161 in different directions in accordance with its wavelength components. In other words, the detection light is spatially dispersed by the dispersion element 161 in accordance with its wavelengths. The spectrally separated detection light enters the convergent lens 163 and converges at different positions in accordance with its wavelength components. Part (light in a specific wavelength band) of the detection light converged by the convergent lens 163 enters the detector 165 through the slit 164. More specifically, of the detection light reaching the slit 164, only the detection light having a wavelength component in a wavelength band that depends on the aperture width (slit width) of the slit 164 selectively passes through the slit 164 and enters the detector 165.

The detector 165 converts the entering light into an electrical signal reflecting its light intensity and outputs the electrical signal. The electrical signal output from the detector 165 is input to and processed by the fluorescence separation arithmetic processing unit 170.

During the spectral detection, the slit 164 is fixed to a constant aperture width (slit width). The aperture width of the slit 164 is adjusted in advance so that the detection light is detected by the detector 165 with a sufficiently high intensity. The aperture width of the slit 164 determines the width of the wavelength band of the light to be detected by the detector 165. In other words, the aperture width of the slit 164 means the wavelength resolution in the spectral detection.

The dispersion element 161 is digitally rotated by the rotary device 162 by a predetermined shift amount in one direction within a predetermined angular range. Accordingly, the wavelength band of light to be transmitted through the slit 164 is shifted by a predetermined shift amount in one direction within a predetermined wavelength region. The shift direction of the wavelength band is arbitrary and depends on the rotational direction of the dispersion element 161. Namely, the wavelength band may be shifted from the short wavelength side to the long wavelength side or vice versa. Hence, the light to be detected by the detector 165 is wavelength-swept. The wavelength region of the wavelength sweep (sweep width) depends on the angular range of the dispersion element 161, which is rotated by the rotary device 162.

Fluorescence is usually very weak. To disperse fluorescence by the dispersion element 161 for the purpose of spectral detection is very disadvantageous to fluorescence detection.

In view of this situation, in spectral detection, this embodiment is directed to detection of fluorescence with a sufficiently high intensity in accordance with the known fluorescence characteristics and the sensitivity of the detector 165.

Figure 2:
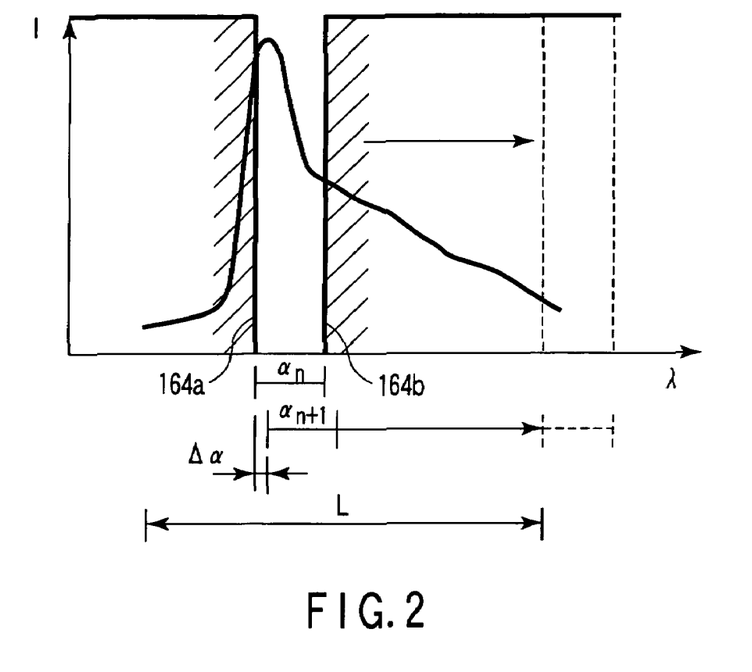
FIG. 2 shows the typical fluorescence characteristics of a fluorescence reagent, the wavelength band of light detected by a detector, and a wavelength region in which the wavelength band is shifted in spectral detection according to the first embodiment.

FIG. 2 shows the typical fluorescence characteristics of a fluorescence reagent, the wavelength band of light detected by the detector, and a wavelength region in which the wavelength band is shifted in spectral detection according to the this embodiment. The typical value of a wavelength region L is usually set at the central wavelength of the wavelength band. The typical value of the wavelength band may be an arbitrary value in the wavelength band, and is set with reference to the lower limit of the wavelength band in FIG. 2.

Referring to FIG. 2, the wavelength band is shifted digitally by a predetermined shift amount from the short wavelength side to the long wavelength side, $\alpha n$ indicates a wavelength band after an nth shift motion, and $\Delta\alpha$ indicates the shift amount (wavelength shift amount) of one shift motion in the wavelength band. The lower limit of the wavelength band $\alpha n$ corresponds to the position of the light-shielding plate 164$a$ of the slit 164, and its upper limit corresponds to the position of the light-shielding plate 164$b$ of the slit 164. The width of the wavelength band $\alpha n$ is constant regardless of the value of n. The wavelength shift amount $\Delta\alpha$ corresponds to the shift amount of the rotation of the dispersion element 161.

In this embodiment, as shown in FIG. 2, the shift amount $\Delta\alpha$ of the wavelength band is set smaller than the width of the wavelength band. When the width of the wavelength band $\alpha n$ is expressed as $|\alpha|$ for the sake of convenience, $\Delta\alpha<|\alpha|$ is established. The width $|\alpha|$ of the wavelength band $\alpha n$ is set by the aperture width of the slit 164 so that the detector 165 detects light with a sufficiently high strength in accordance with the known fluorescence characteristics and the sensitivity of the detector 165.

The width $|\alpha|$ of the wavelength band $\alpha n$ may be set at a comparatively large value to obtain a sufficiently high signal strength. Considering the detection accuracy, the wavelength shift amount $\Delta\alpha$ of the wavelength band $\alpha n$ may be set at a very small value. Regarding the width $|\alpha|$ of the wavelength band $\alpha n$ and the wavelength shift amount $\Delta\alpha$, for example, $\Delta\alpha=2$ nm for $|\alpha|=10$ nm or $\Delta\alpha=5$ nm for $|\alpha|=50$ nm is set. Naturally, the values of $|\alpha|$ and $\Delta\alpha$ are not limited to them, but may be set appropriately within a range where $\Delta\alpha<|\alpha|$ is satisfied by considering the measurement conditions and the like.

Figure 3:
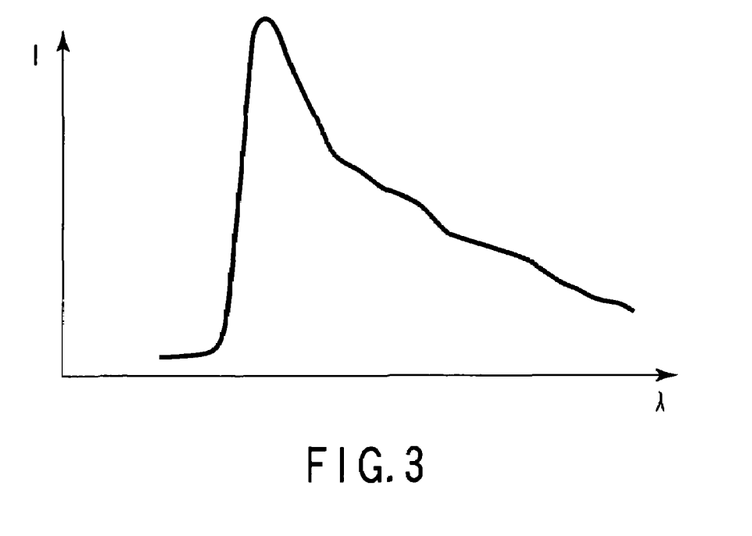
FIG. 3 shows a fluorescence profile obtained by spectral detection according to the first embodiment.

When the width $|\alpha|$ of the wavelength band and the wavelength shift amount $\Delta\alpha$ are set in this manner, light is measured with a sufficiently high strength. Even when the wavelength resolution is not high, the change amount of the fluorescence intensity based on the wavelength shift amount $\Delta\alpha$ is detected very accurately. Thus, as shown in FIG. 3, an accurate fluorescence profile is obtained. The system or obtained profile data may be calibrated on the basis of the characteristics of the system or the obtained fluorescence characteristics.

The separation arithmetic process by the fluorescence separation arithmetic processing unit 170 will be described with reference to FIGS. 4 and 5.

Figure 4:
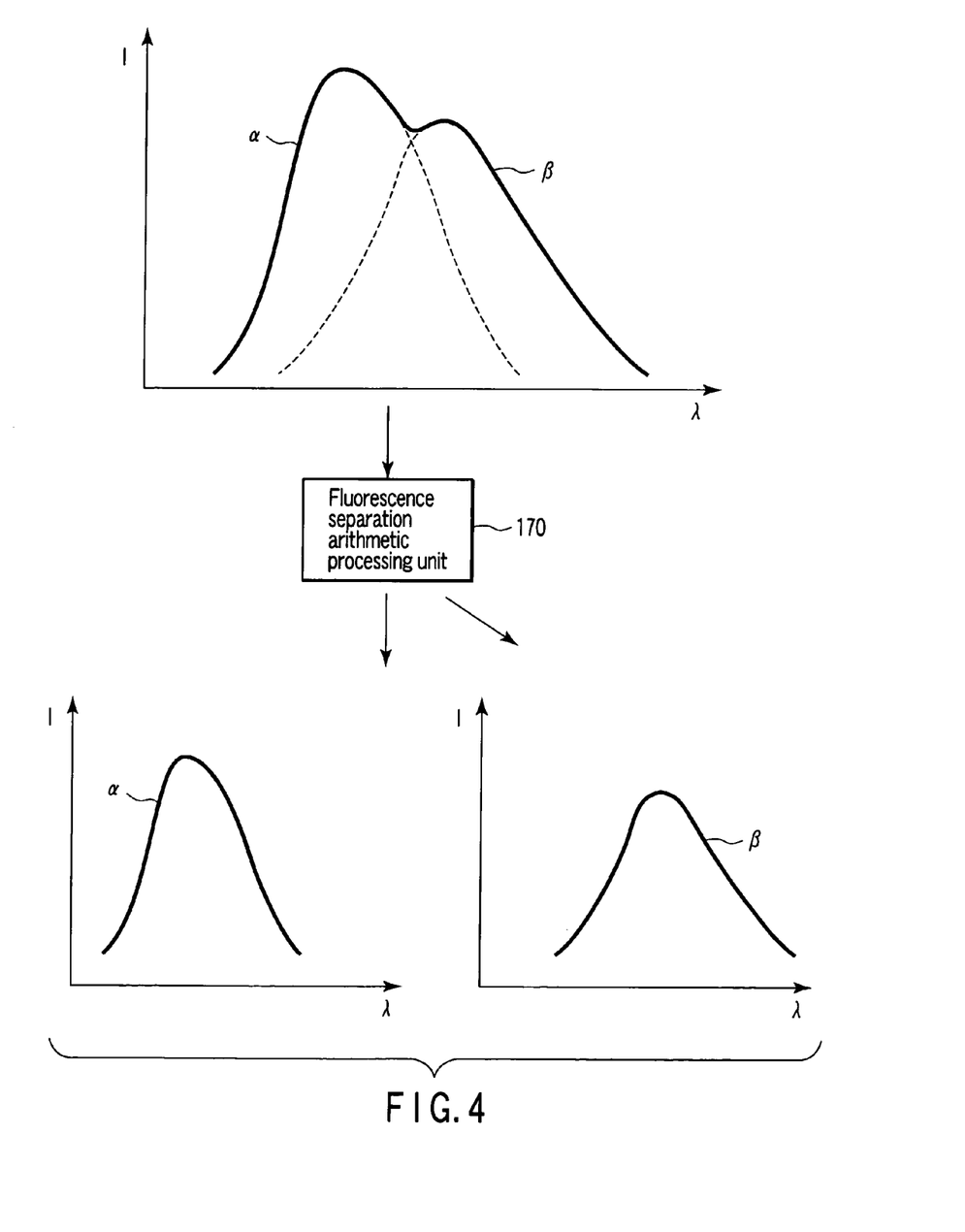
FIG. 4 shows a fluorescence profile including two fluorescence components α and β obtained by spectral detection according to the first embodiment, and the fluorescence profiles of the two fluorescence components α and β.

FIG. 4 shows a fluorescence profile including two fluorescence components $\alpha$ and $\beta$ obtained by spectral detection according to the first embodiment, and the fluorescence profiles of the two fluorescence components $\alpha$ and $\beta$. FIG. 5 shows a fluorescence spectral image $\gamma$ in which the two fluorescence components $\alpha$ and $\beta$ are stacked in the direction of a wavelength axis $\lambda$, and the fluorescence images of the two fluorescence components $\alpha$ and $\beta$.

The acquired fluorescence profile shown in the upper portion of FIG. 4 is separated by separation arithmetic operation of the fluorescence separation arithmetic processing unit 170 into the fluorescence profile of the component $\alpha$ and the fluorescence profile of the component $\beta$, which are shown in the lower portion of FIG. 4. This separation arithmetic operation may be performed by preparing known reference data for each of the fluorescence components $\alpha$ and $\beta$. Alternatively, assuming that the acquired fluorescence profile includes the two fluorescence components $\alpha$ and $\beta$, the separation arithmetic operation may be performed by approximation through repetitive calculation while estimating the profiles of the fluorescence components $\alpha$ and $\beta$. The individual fluorescence profiles $\alpha$ and $\beta$ are extracted from the spectrally detected fluorescence characteristics, as shown in the lower portion of FIG. 4.

Figure 5:
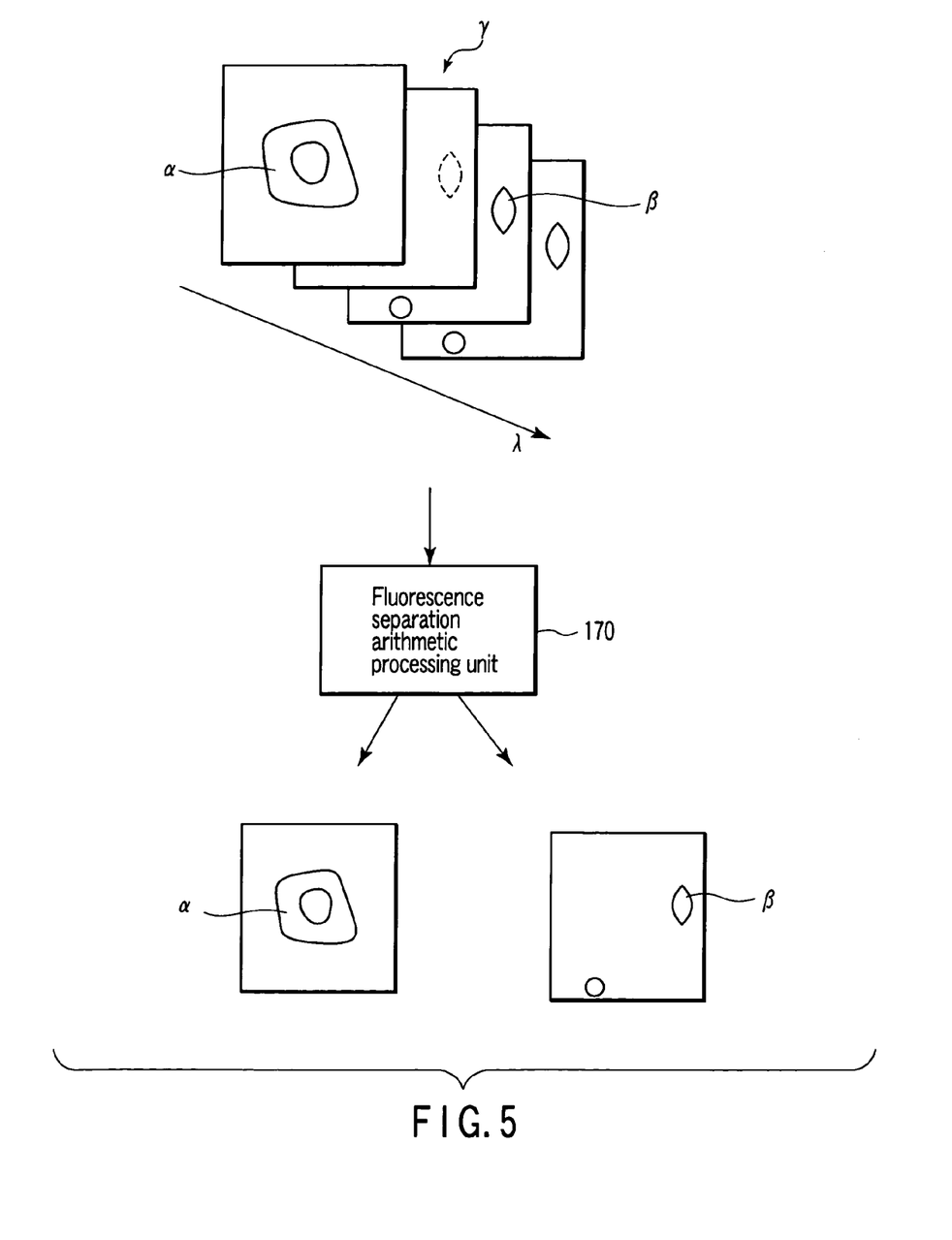
FIG. 5 shows a fluorescence spectral image γ in which the two fluorescence components α and β are stacked in the direction of a wavelength axis λ, and the fluorescence images of the two fluorescence components α and β.

This scheme may be similarly applied to a fluorescence spectral image $\gamma$ shown in the upper portion of FIG. 5. More specifically, each pixel of each image of the fluorescence spectral image $\gamma$ may be subjected to an arithmetic process shown in FIG. 4 to obtain the respective fluorescence images of the two fluorescence components α and β shown in the lower portion of FIG. 5.

According to this embodiment, the width of the wavelength band, which means the wavelength resolution in spectral detection, is set comparatively widely to detect very weak fluorescence from the sample with a sufficiently high strength. The wavelength shift amount is set to be much smaller than the width of the wavelength band to detect the fluorescence profile very accurately. The profile to be detected is a relative one including an overlapping portion. The change amount of the fluorescence characteristics is acquired in more detail from the obtained profile.

Furthermore, the obtained fluorescence profile, which is very accurate, is subjected to separation arithmetic operation by the fluorescence separation arithmetic processing unit to obtain fluorescence information (fluorescence spectral image or fluorescence characteristic data) of each fluorescence component. Even if the fluorescence peaks of two fluorescence components are close to each other and large cross talk is present between the fluorescence information on the two fluorescence components, the fluorescence information, i.e., fluorescence spectral image or fluorescence characteristic data, of each of the two fluorescence components is observed appropriately.

Second Embodiment

Fluorescence is usually very weak. To disperse fluorescence by the dispersion element 161 for the purpose of spectral detection is very disadvantageous to fluorescence detection. The color of fluorescence tends to fade upon application of the excitation light. If the application time of the excitation light is prolonged, the color of some fluorescence may fade, and accurate fluorescence characteristics cannot be measured.

In view of this situation, in spectral detection, this embodiment is directed to detection of fluorescence with a sufficiently high intensity in accordance with the known fluorescence characteristics and the sensitivity of the detector 165, and spectral detection at a comparatively high speed.

The apparatus arrangement of a laser scanning type confocal microscope according to the second embodiment is completely the same as that of the first embodiment.

Figure 6:
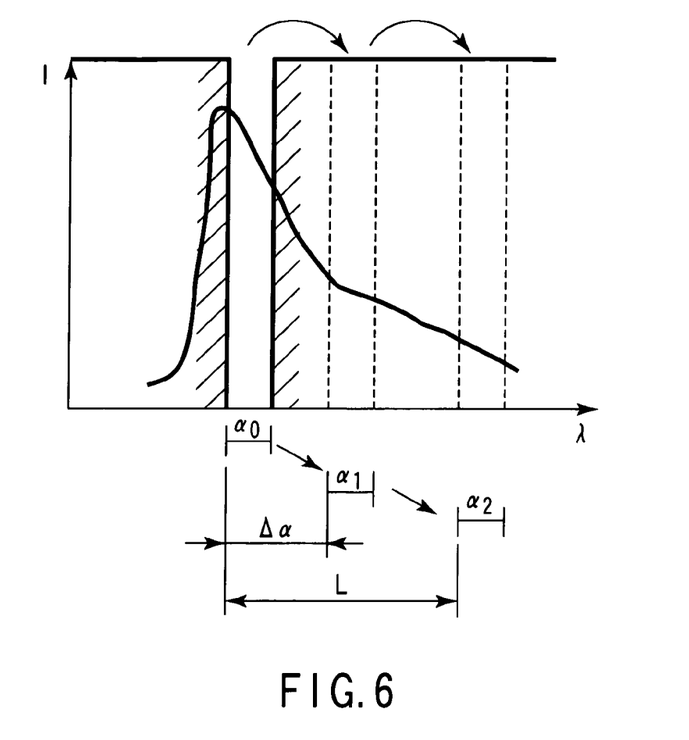
FIG. 6 shows the typical fluorescence characteristics of a fluorescence reagent, the wavelength band of light detected by a detector, and a wavelength region in which the wavelength band is shifted in spectral detection according to the second embodiment of the present invention.

FIG. 6 shows the typical fluorescence characteristics of a fluorescence reagent, the wavelength band of light detected by a detector, and a wavelength region in which the wavelength band is shifted in spectral detection according to the second embodiment. The typical value of a wavelength region L is usually set at the central wavelength of the wavelength band. The typical value of the wavelength band may be an arbitrary value in the wavelength band, and is set with reference to the lower limit of the wavelength band in FIG. 6.

Referring to FIG. 6, the wavelength band is shifted digitally every predetermined shift amount from the short wavelength side to the long wavelength side, $\alpha n$ indicates a wavelength band after an nth shift motion, and $\Delta\alpha$ indicates the shift amount (wavelength shift amount) of one shift motion in the wavelength band. The lower limit of the wavelength band $\alpha n$ corresponds to the position of a light-shielding plate 164a of a slit 164, and its upper limit corresponds to the position of a light-shielding plate 164b of the slit 164. The width of the wavelength band $\alpha n$ is constant regardless of the value of n. The wavelength shift amount $\Delta\alpha$ corresponds to the shift amount of the rotation of the dispersion element 161.

In this embodiment, as shown in FIG. 6, the shift amount $\Delta\alpha$ of the wavelength band is set larger than the width of the wavelength band. When the width of the wavelength band $\alpha n$ is expressed as $|\alpha|$ for the sake of convenience, $\Delta\alpha > |\alpha|$ is established. The width $|\alpha|$ of the wavelength band $\alpha n$ is set by the aperture width of the slit 164 in the same manner as in the first embodiment so that a detector 165 detects light with a sufficiently high strength in accordance with the known fluorescence characteristics and the sensitivity of the detector 165.

Regarding the width $|\alpha|$ of the wavelength band $\alpha n$ and the wavelength shift amount $\Delta\alpha$, for example, $\Delta\alpha = 30$ nm for $|\alpha| = 10$ nm or $\Delta\alpha = 50$ nm for $|\alpha| = 15$ nm is set. Naturally, the values of $|\alpha|$ and $\Delta\alpha$ are not limited to them, but may be set appropriately within a range where $\Delta\alpha > |\alpha|$ is satisfied by considering the measurement conditions and the like.

This embodiment is effective when, e.g., the two fluorescence peaks are rather separate from each other and large cross talk is present between their feet. The wavelength shift amount $\Delta\alpha$ may be set at such a value that the peak change between the two peaks can be detected.

Figure 7:
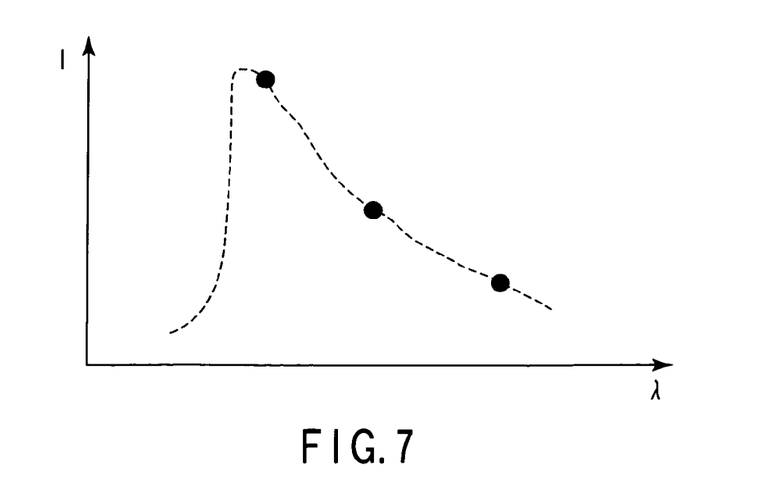
FIG. 7 shows information at discontinuous measurement points and an entire fluorescence profile obtained by interpolation in spectral detection according to the second embodiment.

When the width $|\alpha|$ of the wavelength band and the wavelength shift amount $\Delta\alpha$ are set in this manner, light is measured with a sufficiently high strength. As expressed by full circles in FIG. 7, due to the wavelength shift amount $\Delta\alpha$, the number of measurement points along the wavelength axis decreases with respect to the fluorescence characteristics. Accordingly, spectral detection is performed within a short period of time, i.e., at a high speed. This embodiment is very effective for a fluorescent dye that fades very soon. With this scheme, information is acquired at only discontinuous measurement points. If the non-measured portions (a broken line in FIG. 7) are interpolated by using the information obtained at the discontinuous measurement points, the entire fluorescence profile is estimated.

The obtained fluorescence profile may be subjected to a separation arithmetic process by a fluorescence separation arithmetic processing unit 170 in the same manner as in the first embodiment.

According to this embodiment, the outline of the fluorescence characteristics of the sample is detected simply. Also, the individual fluorescence characteristics are observed at once by the fluorescence separation arithmetic operation in the same manner as in the first embodiment.

Third Embodiment

Figure 8:
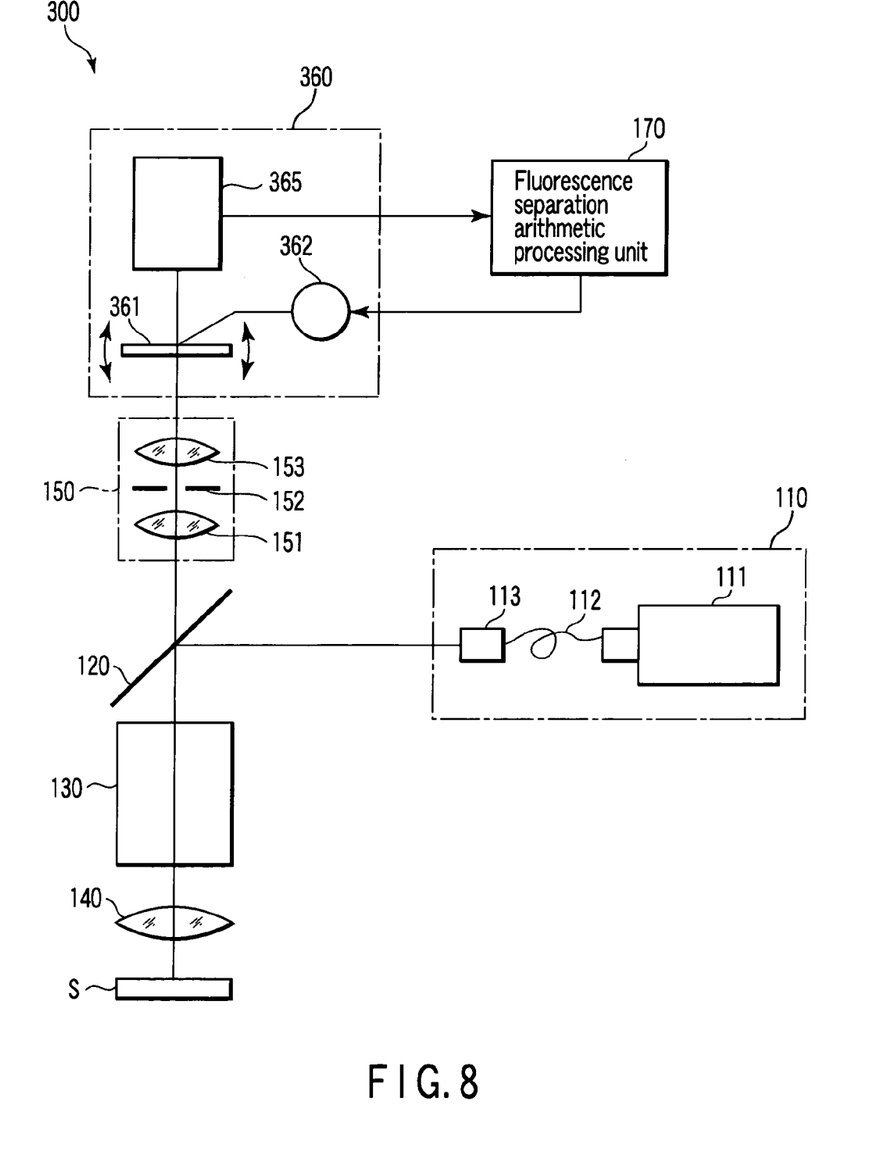
FIG. 8 schematically shows the arrangement of a laser scanning type confocal microscope according to the third embodiment of the present invention.

FIG. 8 schematically shows the arrangement of a laser scanning type confocal microscope according to the third embodiment of the present invention. Referring to FIG. 8, members that are indicated by the same reference numerals as those shown in FIG. 1 are similar members, and a detailed description thereof will be omitted. The laser scanning type confocal microscope according to this embodiment is different from that of the first embodiment in only the spectral detection device. Except for this, the arrangement of the third embodiment is the same as that of the first embodiment.

As shown in FIG. 8, a spectral detection device 360 of a laser scanning type confocal microscope 300 according to this embodiment has a bandpass filter 361 that selectively transmits light in a predetermined wavelength band, rotary means or a rotary device 362 for rotating the bandpass filter 361 about an axis perpendicular to the optical axis, and a detector 165 for detecting light transmitted through the bandpass filter 361.

The laser scanning type confocal microscope according to this embodiment operates in completely the same manner as the laser scanning type confocal microscope of the first embodiment except for the spectral detection device. In other words, excitation light is applied to a sample S, detection light generated by the sample S is guided to the spectral detection device, and information detected by the spectral detection device is processed in the same manner as in the first embodiment.

Figure 9:
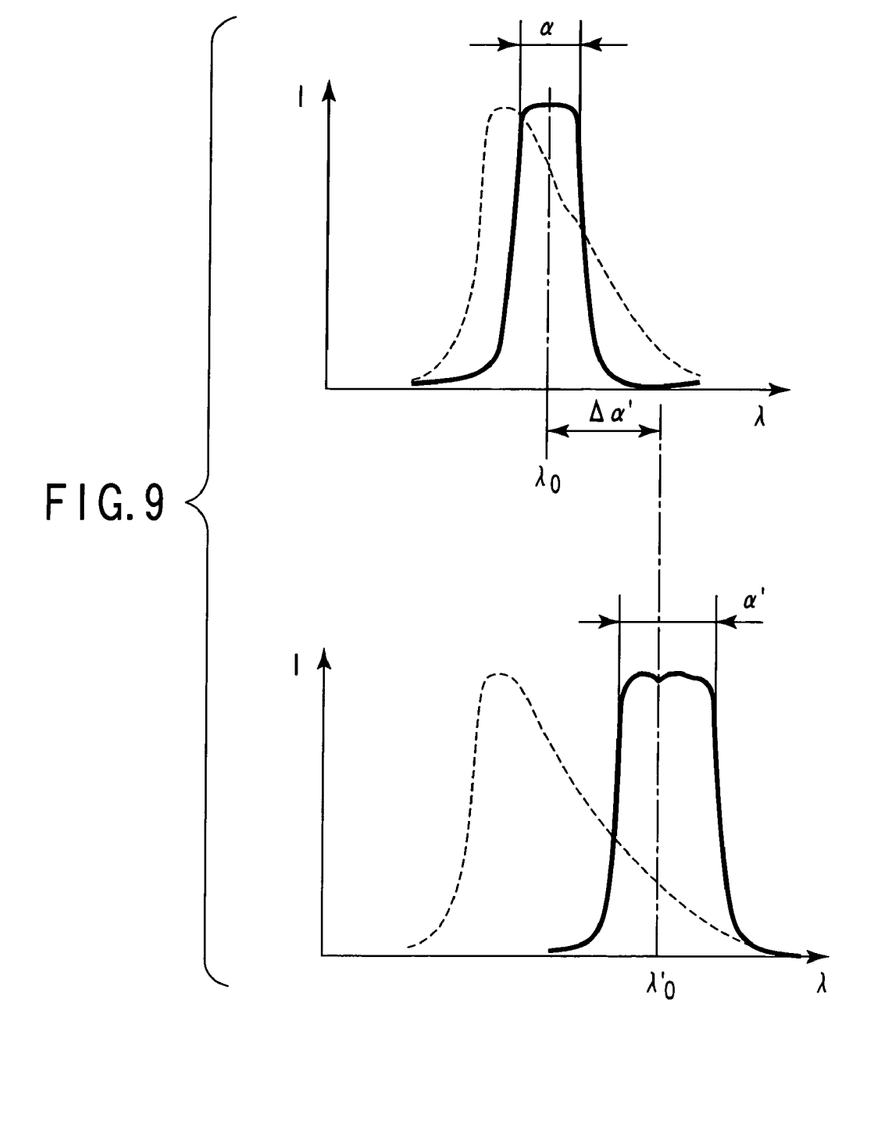
FIG. 9 shows the typical fluorescence characteristics (broken lines) of a fluorescence reagent and the transmission characteristics (solid lines) of the band-bass filter in FIG. 8.

FIG. 9 shows the typical fluorescence characteristics (broken lines) of a fluorescence reagent and the transmission characteristics (solid lines) of the band-bass filter. The transmission characteristics of the bandpass filter 361 depend on the incident angle of light, and are precisely designed in advance in accordance with the anticipated incident angle of light. If the incident angle at which light enters the bandpass filter 361 shifts from the designed value, the transmission characteristics change accordingly.

The upper portion of FIG. 9 shows the transmission characteristics of the bandpass filter 361 with respect to the designed incident angle, and its lower portion shows the transmission characteristics of the bandpass filter 361 with respect to an incident angle that shifts from the designed value.

When the incident angle has the designed value, the bandpass filter 361 transmits light in a wavelength band having a central wavelength $\lambda 0$ and width $\alpha$. The transmission characteristics of the bandpass filter 361 depend on the interference film of the bandpass filter 361. The central wavelength $\lambda 0$ and a width $\alpha 0$ of the wavelength band that transmits light are freely set by the interference film. As the bandpass filter 361, one which has a transmission wavelength band with the width $\alpha 0$ matching the fluorescence as the detection target is prepared. The width $\alpha 0$ of the transmission wavelength band serves in the same manner as the slit 164 in the first and second embodiments.

When the bandpass filter 361 is rotated by the rotary device 362 and is inclined from the designed use state, the incident angle at which light enters the bandpass filter 361 shifts from the designed value. Thus, the bandpass filter 361 transmits light in a wavelength band having a central wavelength $\lambda 0'$ and width $\alpha'$, as shown in the lower portion of FIG. 9. In other words, in accordance with the rotation of the bandpass filter 361, the central wavelength of the transmission wavelength band of the transmission characteristics of the bandpass filter 361 shifts from $\lambda 0$ to $\lambda 0'$, and the width of the wavelength band changes from $\alpha$ to $\alpha'$. This change in transmission characteristics occurs linearly with respect to the incident angle. A wavelength shift amount $\Delta \alpha'$ of the central wavelength of the transmission wavelength band depends on the rotational angle of the bandpass filter 361.

Therefore, (the central wavelength of) the transmission band is changed by controlling the rotational angle of the bandpass filter 361, in other words, the inclination of the bandpass filter 361 with respect to the optical axis by the rotary device 362. Thus, the wavelength of light to be detected by the detector 365 is changed.

Namely, when the bandpass filter 361 is rotated by the rotary device 362 digitally every predetermined shift amount in one direction within a predetermined angular range, light to be detected by the detector 365 is wavelength-swept. The shift direction of the wavelength band of the light to be detected by the detector 365 depends on the rotational direction of the bandpass filter 361. The wavelength band may be shifted from the short wavelength side to the long wavelength side or vise versa. The wavelength region (sweeping width) of wavelength sweep depends on the angular range of the bandpass filter 361 that is rotated by the rotary device 362.

The wavelength shift amount $\Delta \alpha'$ may be determined in accordance with the fluorescence material in the sample or necessary information accuracy in the same manner as in the first or second embodiment.

As apparent from the above description, in the third embodiment, the bandpass filter 361 serves as spectroscopic means or a spectroscopic element for spectrally separating detection light, and light extracting means or a light extracting portion for extracting light in a wavelength band having an arbitrary width from the light spectrally separated by the spectroscopic element. The rotary device 362 serves as wavelength band shifting means or a wavelength band shifting unit for shifting the wavelength band of light to be extracted by the bandpass filter 361. The rotary device 362 comprises, e.g., a galvanometer or stepping motor but is not limited to this.

According to this embodiment, the weak fluorescence strength is not dispersed by the dispersion element such as a diffraction grating. Thus, the fluorescence is detected with a small loss and a very high strength. Note that the shift of the transmission wavelength band of the bandpass filter 361 with respect to a change in incident angle is small as compared to the shift of the wavelength band in the first and second embodiments. Accordingly, the wavelength region (sweep width) of wavelength sweep is narrower than in the first and second embodiments. For this reason, the third embodiment is suitable to detailed spectral detection in a comparatively narrow wavelength region (e.g., about 30 nm to 40 nm, preferably about 50 nm to 60 nm).

When the bandpass filter 361 is used in an inclined state, its transmission characteristics slightly change from the designed transmission characteristics. In this case, preferably, the transmission characteristics of the bandpass filter 361 with respect to the incident angle may be measured and calculated in advance to calibrate data obtained by spectral detection. For example, with respect to the designed incident angle and inclination angle of the bandpass filter 361, if the relative change in total fluorescence amount obtained in the transmission wavelength band is prepared as calibration ratio data, detection data is calibrated easily.

The embodiments of the present invention have been described above with reference to the views of the accompanying drawing. However, the present invention is not limited to these embodiments, and may be variously changed or modified within the spirit and scope of the invention.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A light scanning type confocal microscope comprising:
a light source unit that projects an excitation light beam;
a scanning optical system that scans the excitation light beam;
an objective lens that applies the excitation light beam to a sample;

a separation optical element that separates the excitation light applied to the sample and detection light generated by the sample upon application of the excitation light;

a confocal detection unit that obtains a confocal effect; and a spectral detection device that spectrally detects the detection light, the spectral detection device including: a spectroscopic element that spectrally separates the detection light, a light extracting unit that extracts light in a wavelength band having an arbitrary width from the detection light spectrally separated by the spectroscopic element, a detector that detects the light extracted by the light extracting unit, and a wavelength band shifting unit that shifts a wavelength band of light to be extracted by the light extracting unit;

wherein a shift amount of the wavelength band by the wavelength band shifting unit is smaller than a width of the wavelength band.

2. A microscope according to claim 1, further comprising a fluorescence separation arithmetic processing unit that separately calculates fluorescence information corresponding to spectral components of respective fluorescence types from fluorescence information obtained by the spectral detection device.

3. A microscope according to claim 2, wherein the spectroscopic element comprises a dispersion element that deflects the detection light in different directions in accordance with wavelengths of the light.

4. A microscope according to claim 2, wherein the light extracting unit comprises a mechanical variable aperture having a changeable aperture width, and wherein light-shielding plates that define the aperture determine upper and lower limits of the wavelength band of light to be extracted.

5. A microscope according to claim 3, wherein the wavelength band shifting unit comprises a rotary device that rotates the dispersion element about an axis perpendicular to an optical axis.

6. A light scanning type confocal microscope comprising:

a light source unit that projects an excitation light beam;

a scanning optical system that scans the excitation light beam;

an objective lens that applies the excitation light beam to a sample;

a separation optical element that separates the excitation light applied to the sample and detection light generated by the sample upon application of the excitation light;

a confocal detection unit that obtains a confocal effect;

a spectral detection device that spectrally detects the detection light, the spectral detection device including: a spectroscopic element that spectrally separates the detection light and that comprises a bandpass filter that selectively transmits light in a predetermined wavelength band, a detector, and a wavelength band shifting unit that shifts a wavelength band of light to be detected by the detector, the wavelength band shifting unit comprising a rotary device that rotates the bandpass filter about an axis perpendicular to an optical axis; and a fluorescence separation arithmetic processing unit that separately calculates fluorescence information corresponding to spectral components of respective fluorescence types from fluorescence information obtained by the spectral detection device; and wherein a shift amount of the wavelength band by the wavelength band shifting means is smaller than a width of the wavelength band.

7. A light scanning type confocal microscope comprising:

a light source unit for projecting an excitation light beam;

a scanning optical system for scanning the excitation light beam;

an objective lens for applying the excitation light beam to a sample;

a separation optical element for separating the excitation light applied to the sample and detection light generated by the sample upon application of the excitation light;

a confocal detection unit for obtaining a confocal effect; and spectral detecting means for spectrally detecting the detection light, the spectral detecting means including: light extracting means for extracting light in a wavelength band having an arbitrary width from the detection light, detecting means for detecting the light extracted by the light extracting means, and wavelength band shifting means for shifting a wavelength band of light to be extracted by the light extracting means;

wherein a shift amount of the wavelength band by the wavelength band shifting means is smaller than a width of the wavelength band.

8. A microscope according to claim 7, further comprising fluorescence separation arithmetic processing means for separately calculating fluorescence information corresponding to spectral components of respective fluorescence types from fluorescence information obtained by the spectral detecting means.

9. A light scanning type confocal microscope comprising:

a light source unit that projects an excitation light beam;

a scanning optical system that scans the excitation light beam;

an objective lens that applies the excitation light beam to a sample;

a separation optical element that separates the excitation light applied to the sample and detection light generated by the sample upon application of the excitation light;

a confocal detection unit that obtains a confocal effect;

a spectral detection device that spectrally detects the detection light, the spectral detection device including: a dispersion element that deflects the detection light in different directions in accordance with wavelengths thereof, a light extracting unit that has an aperture that transmits light in a wavelength band from the detection light spectrally separated by the dispersion element, and a wavelength band shifting unit that shifts a wavelength band of light to be transmitted through the light extracting unit by a shift amount smaller than a width of the wavelength band; and a fluorescence separation arithmetic processing unit that separately calculates fluorescence information corresponding to spectral components of respective fluorescence types from fluorescence spectral information obtained by the spectral detection device overlapping with a step smaller than the width of the wavelength band.

10. A microscope according to claim 4, wherein the spectroscopic element comprises a diffraction grating that deflects the detection light in different directions in accordance with wavelengths of the light.

11. A microscope according to claim 5, wherein the dispersion element comprises a diffraction grating.

12. A microscope according to claim 8, further comprising a dispersion element that deflects the detection light in different directions in accordance with wavelengths of the light, wherein the light extracting means extracts the light in the wavelength band having the arbitrary width from the detection light deflected in different directions by the dispersion element.

13. A microscope according to claim 8, wherein the light extracting means comprises a mechanical variable aperture having a changeable aperture width, and wherein light-shielding plates that define the aperture determine upper and lower limits of the wavelength band of light to be extracted.

14. A microscope according to claim 12, wherein the wavelength band shifting means comprises a rotary device that rotates the dispersion element about an axis perpendicular to an optical axis.

15. A microscope according to claim 13, further comprising a diffraction grating that deflects the detection light in different directions in accordance with wavelengths of the light, wherein the light extracting means extracts the light in the wavelength band having the arbitrary width from the detection light deflected in different directions by the diffraction grating.

16. A microscope according to claim 14, wherein the dispersion element comprises a diffraction grating.

* * * * *